(12) United States Patent
Su et al.

(10) Patent No.: US 11,857,177 B2
(45) Date of Patent: Jan. 2, 2024

(54) METHOD FOR SUTURING ALONG PATH AND APPARATUS THEREOF

(71) Applicant: JIANGNAN UNIVERSITY, Wuxi (CN)

(72) Inventors: Junqiang Su, Wuxi (CN); Honglian Cong, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 18/056,140

(22) Filed: Nov. 16, 2022

(65) Prior Publication Data

US 2023/0149012 A1 May 18, 2023

(30) Foreign Application Priority Data

Nov. 17, 2021 (CN) .......................... 202111361111.1

(51) Int. Cl.
*A61B 17/04* (2006.01)
*A61B 17/00* (2006.01)
(Continued)

(52) U.S. Cl.
CPC ...... *A61B 17/0469* (2013.01); *A61B 17/0491* (2013.01); *A61B 2017/00367* (2013.01);
(Continued)

(58) Field of Classification Search
CPC ............ A61B 17/0469; A61B 17/0491; A61B 2017/00367; A61B 2017/047;
(Continued)

(56) References Cited

U.S. PATENT DOCUMENTS 5,782,844 A * 7/1998 Yoon .................... A61B 17/064
606/139
5,810,851 A 9/1998 Yoon
(Continued)

FOREIGN PATENT DOCUMENTS

CN 105960208 A 9/2016
CN 211355655 U 8/2020
(Continued)

OTHER PUBLICATIONS

Notice of Grant issued in Chinese Patent Application No. 20211136111.1; dated Jul. 13, 2022; 3 pgs.

*Primary Examiner* — Tuan V Nguyen
(74) *Attorney, Agent, or Firm* — HAUPTMAN HAM, LLP

(57) ABSTRACT

An apparatus for suturing includes an inner strut, a spiral suturing needle, a driving mechanism, a recovery mechanism, a suture-taking-up mechanism, and a suture-feeding mechanism. Grooves are distributed on periphery with respect to an axial direction of the inner strut, a path of the groove is consistent with a path of a metallic stent to be sutured, and a width of the groove matches an outer diameter of the spiral suturing needle; the spiral suturing needle is an elastic retractable structure and a length of the spiral suturing needle without deformation is longer than a length of the path of the groove, and a suturing needle tip is arranged on a head portion of the spiral suturing needle and a suture-piercing hole is arranged on a tail portion of the spiral suturing needle.

7 Claims, 3 Drawing Sheets

(51) Int. Cl.
  *A61B 17/06*     (2006.01)
  *A61F 2/07*      (2013.01)
(52) U.S. Cl.
  CPC . *A61B 2017/047* (2013.01); *A61B 2017/0475* (2013.01); *A61B 2017/0479* (2013.01); *A61B 2017/0496* (2013.01); *A61B 2017/0498* (2013.01); *A61B 2017/06076* (2013.01); *A61F 2002/075* (2013.01); *A61F 2240/001* (2013.01)
(58) Field of Classification Search
  CPC .... A61B 2017/0475; A61B 2017/0479; A61B 2017/0496; A61B 2017/0498; A61B 2017/06076; A61F 2002/075; A61F 2240/001
  See application file for complete search history.

(56) References Cited

U.S. PATENT DOCUMENTS

| | | | |
|---|---|---|---|
| 5,820,631 A | | 10/1998 | Nobles |
| 2009/0240264 A1* | | 9/2009 | Tuval ................. A61B 17/0469 606/148 |
| 2012/0035654 A1 | | 2/2012 | Belson |
| 2016/0007993 A1 | | 1/2016 | Smith et al. |
| 2019/0343529 A1* | | 11/2019 | Smith .............. A61B 17/06066 |
| 2020/0305876 A1* | | 10/2020 | Smith ................ A61B 17/0469 |

FOREIGN PATENT DOCUMENTS

| | | |
|---|---|---|
| CN | 112568950 A | 3/2021 |
| CN | 113556982 A | 10/2021 |
| CN | 114159187 B | 8/2022 |
| WO | 2007098212 A2 | 8/2007 |

\* cited by examiner

METHOD FOR SUTURING ALONG PATH AND APPARATUS THEREOF

RELATED APPLICATIONS

The present application claims priority from Chinese Application Number 202111361111.1, filed Nov. 17, 2021, the disclosure of which is hereby incorporated by reference herein in its entirety.

TECHNICAL FIELD

The present disclosure relates to the technical field of special suturing, and in particular to a method for suturing along a path and an apparatus thereof.

BACKGROUND

In medical instruments and the related fields, there is a need for artificial blood vessels, and the like, for the adjuvant therapy and rehabilitation plerosis, and the utilizations of the artificial blood vessels include implantations of the artificial blood vessels (similar to coronary stent), hemodialysis, and the like.

Currently, as illustrated in FIG. 2, the main materials for manufacturing an artificial blood vessel 100 include a stent 101, a polymer filtration membrane 102 and a suture 103 configured to suture the two of 101 and 102 together. In view of the structure of the artificial blood vessel 100, the polymer filtration membrane 102 is mainly sutured to form a tubular channel, and then the special metallic alloy stent 101 are arranged according to certain rules and sutured inside the tubular channel, and the polymer filter membrane 102 and the frames 101 are bound together with the surgically used suture 103, resulting in forming the artificial blood vessel 100.

(1) The metallic stents are generally made of memonic alloy materials (such as titanium alloy), which have the characteristics or functions, such as high elasticity, high shrinkage ratio, shape performance. In addition, the stents should be pre-shaped at a high temperature, and the head and tail ends of the stents should be closed to form a multiple-"W"-shaped ring structure like a crown shape, wherein the head and tail ends should be closed at a high temperature.

(2) The apertures of the artificial blood vessels generally range from 1 cm to 5 cm, and the lengths of the artificial blood vessels range from 10 cm to 50 cm. The current suturing process requirements are that: the polymer filter materials must be sutured to form a cylindrical form (hereinafter, referred to as "blood vessel wall"), subsequently the stents are put inside the blood vessel walls, and then the two of the stents and the blood vessel walls can be bound and sutured.

(3) In view of the current situations, at present, the artificial blood vessels can only be sutured manually. The reason is that the stents are pre-formed into three-dimensional "W"-shaped annular objects, and need to be loaded into the "blood vessel walls", and the subsequent suturing operation belongs to the category of 3D suture, and 3D suture technology is a worldwide difficulty, which is basically done by manual suturing.

In reality, with the increasing labor shortage and the sharp rise of labor costs, the industry urgently needs technology or suturing systems that can realize automatic suturing. Although the problem for the automatic suturing of the artificial blood vessels is naturally associated with various kinds of suturing machines, the conflicts between ideals and realities lie in the following.

(1) In view of the mechanical structures of the suturing machines, whether the suturing structure is in a trace of a chain suture or lock suture, all of the suturing tracks can only be completed in cooperation of the needle bar mechanism and the hook set (rotary hook or-looper). However, the diameters of the existing bobbin/hooking mechanisms or the looper mechanisms are in a range of far more than 5 cm, which are too large to fit the existing sewing mechanism into the artificial blood vessels, thereby machine suturing cannot be achieved.

(2) As mentioned above, since the closure of the head end and tail end of the stent must be achieved at a high temperature, the idea of suturing the flatten stent together with the thin film of the filter material, and then rolling up into a cylinder form has no operability.

(3) In order to achieve the objective of displacing the manual suturing, some technicians have explored the utilization of two or more manipulators for suturing, such as a Da Vinci manipulator, this kind of technology may be able to achieve the objectives, however, there is a need for the supports of the robot technology, machine vision technology, and the like, resulting in an extremely high implementation cost (millions of dollars), which is not practical for the sale prices of the artificial blood vessels.

In conclusion, it is necessary to seek for an automatic suturing method and technical solution that can realize the automatic suturing of objects with small diameter such as artificial blood vessels and need to be sutured along the path (i.e., along the path of the stent).

SUMMARY

Technical problems to be solved are as follows: In view of the above technical problems, the present disclosure provides a method for suturing along a path and an apparatus thereof, which can realize the sutures of small-diameter objects prepared by flexible materials along the paths, and solves the problem of difficulties in suturing the artificial blood vessels and similar scenarios along the paths.

Technical solutions are as follows: An apparatus for suturing along a path comprises: an inner strut, a spiral suturing needle, a driving mechanism, a recovery mechanism, a suture-taking-up mechanism, and a suture-feeding mechanism; grooves are distributed on periphery with respect to an axial direction of the inner strut, a path of the groove is consistent with a path of a metallic stent to be sutured, and a width of the groove matches an outer diameter of the spiral suturing needle; the spiral suturing needle is an elastic retractable structure and a length of the spiral suturing needle without deformation is longer than a length of the path of the groove, and a suturing needle tip is arranged on a head portion of the spiral suturing needle and a suture-piercing hole is arranged on a tail portion of the spiral suturing needle; the driving mechanism is detachably arranged at a rear end of the spiral suturing needle, the driving mechanism includes a driving wheel, a needle penetration rod and a variable aperture baffle, and an eccentric through hole is arranged on the driving wheel, and one end of the needle penetration rod is fixedly connected to a center of the driving wheel, the variable aperture baffle is arranged on one side of the needle penetration rod, and a distance between the variable aperture baffle and the driving wheel is equal to a compression length of the spiral suturing needle; the recovery mechanism is detachably arranged at a front end of the spiral suturing needle, the recovery mechanism includes a recovery wheel on which an eccentric through hole is arranged, a thickness of which is equal to a distance between two adjacent helices of the spiral suturing needle without deformation; the suture-taking-up mechanism with a hook-shaped end is arranged along a path direction of the groove; the suture-feeding mechanism is arranged at the tail portion of the spiral suturing needle, the suture-feeding mechanism includes a suture-winding shaft, a spring crimper and a connecting rod, two ends of the connecting rod are respectively connected with the suture-winding shaft and the driving wheel respectively, and the spring line crimper is arranged on the connecting rod.

Optionally, the suture-taking-up mechanism includes a suture-taking-up shaft and a suture-taking-up hook, and a middle portion of the suture-taking-up hook is hinged with the suture-taking-up shaft.

Optionally, a distance between the center of the driving wheel and the eccentric through hole on the driving wheel is equal to a radius of the spiral suturing needle; and a distance between a center of the recovery wheel and the eccentric through hole on the recovery wheel is equal to the radius of the spiral suturing needle.

Optionally, a threaded channel is arranged in the groove.

Optionally, a depth of the groove is greater than ⅔ a length of the outer diameter length of the spiral suturing needle.

Optionally, the suture-taking-up mechanism is arranged at an inflection point of the groove.

Optionally, the inner diameter of the spiral suturing needle is greater than a diameter of a metallic stent.

Optionally, the apparatus further includes a knotting mechanism configured to knot a suture.

The present disclosure further provides a method for suturing a path by utilizing the apparatus. The method comprises the following steps.

In S1, the metallic stent to be sutured is embedded into the groove, and then the inner strut is sheathed inside a sutured material, the driving mechanism is installed at the rear end of the spiral suturing needle and compresses the spiral suturing needle, In S2, the spiral suturing needle is rotated by the driving mechanism, to enable the suturing needle tip to repeat a process of piercing into the sutured material, bypassing a metal wire of the metallic stent, and piercing out the sutured material; so that the compressed spiral suturing needle recoveries elasticity with the rotating action and continuously moving forward along the path of the groove.

In S3, after the spiral suturing needle completes the process along the path, the suturing needle tip is rotated out of the groove, then the action of the driving mechanism is disabled, the recovery mechanism is installed at the front end of the spiral suturing needle, and the suture is provided to the suture-piercing hole by the suture-feeding mechanism.

In S4, the spiral suturing needle is rotated by the recovery mechanism, so that the spiral suturing needle is rotated out of the groove, and the metallic stent and the sutured material is bound by using the suture at the tail portion of the spiral suturing needle.

In S5, the suture is taken up by the suture-taking-up mechanism on the path of the groove, and the suture is tightened by the recovery mechanism and the suture-feeding mechanism, and the taking-up and and tightening operations are repeated.

In S6, after the rear end of the spiral suturing needle is rotated out of the groove, the spiral suturing needle and the recovery mechanism are removed, and two ends of the suture is knotted to complete the suturing along the path.

Optionally, the suture is knotted automatically by the knotting mechanism in S6.

Beneficial effects are that: the spiral suturing needle of the present disclosure is a rotary-advancing-type suturing needle, which can be combined with the driving mechanism. during the suturing process, on the one hand, the spiral suturing needle can advance forward with the suture; on the other hand, the spiral suturing needle can suture along the path, that is, sutures a cylindrical sutured material made of a flexible material similar with textiles together with the metallic stent used for internally strutting. The helix diameter of the spiral suturing needle can be designed to be extremely small (theoretically, as long as larger than the diameter of the metal wire of the metallic stent), and the spiral suturing needle is suturing only along the path of the metallic stent regardless of the diameter of the whole object to be sutured.

The apparatus and method in the present disclosure have the characteristics of simple mechanism and lower cost, and can realize the suturing along the path of small diameter objects made of flexible materials, solve the problem of difficulties in suturing the artificial blood vessels and similar scenarios along the paths, thereby have a high promotion value.

Figure 1:
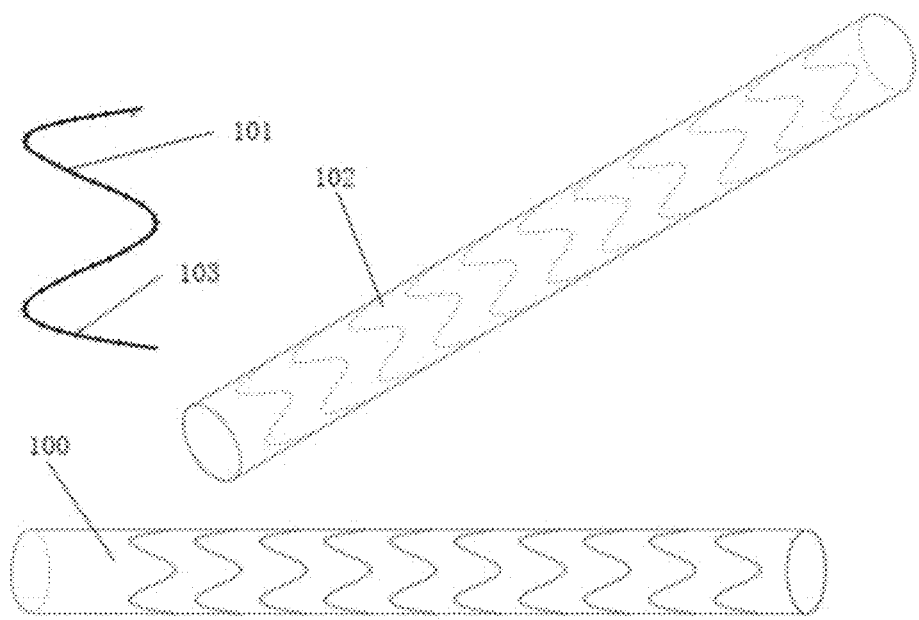
FIG. 1 illustrates a schematic diagram of an artificial blood vessel according to an embodiment of the present disclosure, wherein the reference numerals are represented as follows: 100. Artificial Blood Vessel; 101. Stent; 102. Polymer Filtration Membrane; 103. Suture.

Description of reference numerals is as follows: 1. Inner Strut; 2. Spiral Suturing Needle; 3. Driving mechanism; 4. Recovery mechanism; 5. Suture-taking-up Mechanism; 6. Suture Feeding Mechanism; 11. Groove; 21. Suturing Needle Tip; 22. Suture-piercing Hole; 31. Driving Wheel; 32. Needle Penetration Rod; 33. Variable Aperture Baffle; 51. Suture-taking-up Shaft; 52. Suture-taking-up Hook; 61. Suture-winding Shaft; 62. Spring Crimper; 63. Connecting Rod.

DETAILED DESCRIPTION OF THE EMBODIMENTS

The present disclosure will be further described below with reference to the accompanying drawings and the specific embodiments.

Embodiment 1

Figure 2:
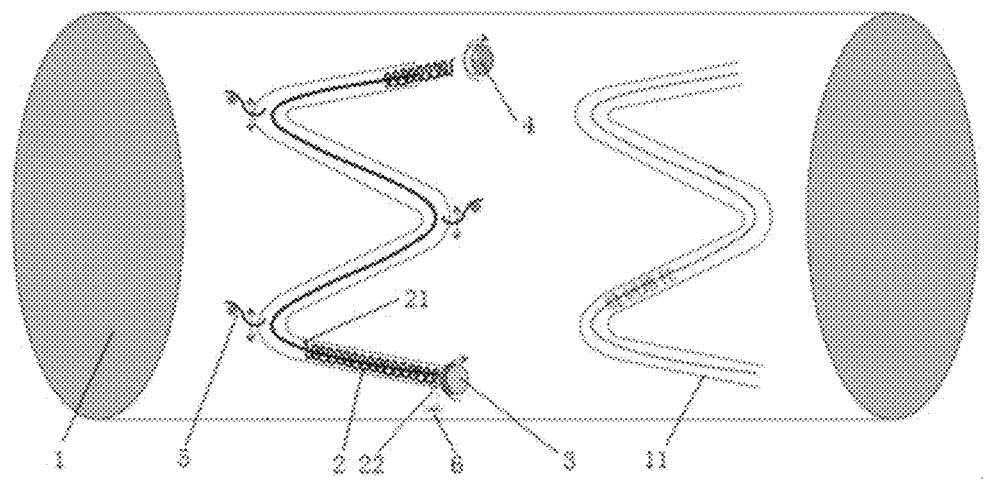
FIG. 2 illustrates a schematic diagram of an apparatus according to an embodiment of the present disclosure.

As illustrated in FIG. 2, provided is an apparatus for suturing along a path. The apparatus comprises an inner strut 1, a spiral suturing needle 2, a driving mechanism 3, a recovery mechanism 4, a suture-taking-up mechanism 5, and a suture-feeding mechanism 6.

The inner strut 1 is in a cylindrical shape with a diameter that is slightly less than the inner diameter of the cylindrical sutured materials to be sutured, and configured to stretch the sutured material. According to the distribution requirements for the metallic stent to be sutured, a binding groove 11 is arranged at periphery with respect to an axial direction of the inner strut 1 to accommodate the metallic stent. wherein, the path of the groove 11 is consistent with the path of the metallic stent, the width of the groove 11 matches the outer diameter of the spiral suturing needle 2, and the depth of the groove 11 is greater than ⅔ the length of the outer diameter of the spiral suturing needle 2, the embedded threaded channel is arranged in the groove 11, which can constrain the spiral suturing needle 2 to advance forward according to the track of the threaded channel.

The spiral suturing needle 2 is an elastic retractable structure and a length of the spiral suturing needle 2 is longer than a length of the path of the groove 11, so that the spiral suturing needle 2 can fill the path of groove 11. The suturing needle tip 21 is arranged on the head portion of the spiral suturing needle 2 and configured to pierce the the sutured material and the suture-piercing hole 22 is arranged on the tail portion of the spiral suturing needle 2 so that the suture can rotate forward with the spiral suturing needle 2 after the suture enters through the suture-piercing hole 22. The inner diameter of the spiral suturing needle 2 is longer than the diameter of a metallic stent and less than the width of the groove 11, so the spiral suturing needle 2 can surround the wire of the metallic stent and advance forward along the threaded channel.

Figure 3:
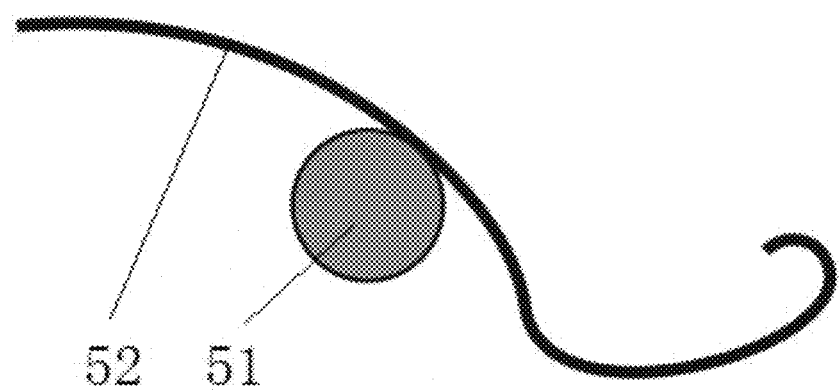
FIG. 3 illustrates a working schematic diagram of a suture-taking-up mechanism according to an embodiment of the present disclosure.
Figure 4:
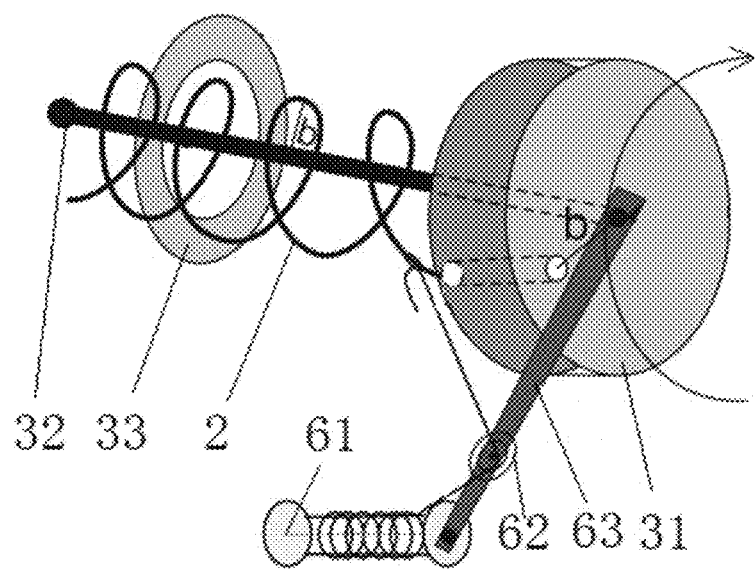
FIG. 4 illustrates a schematic diagram of the driving mechanism and the suture-feeding mechanism according to an embodiment of the present disclosure.
Figure 5:
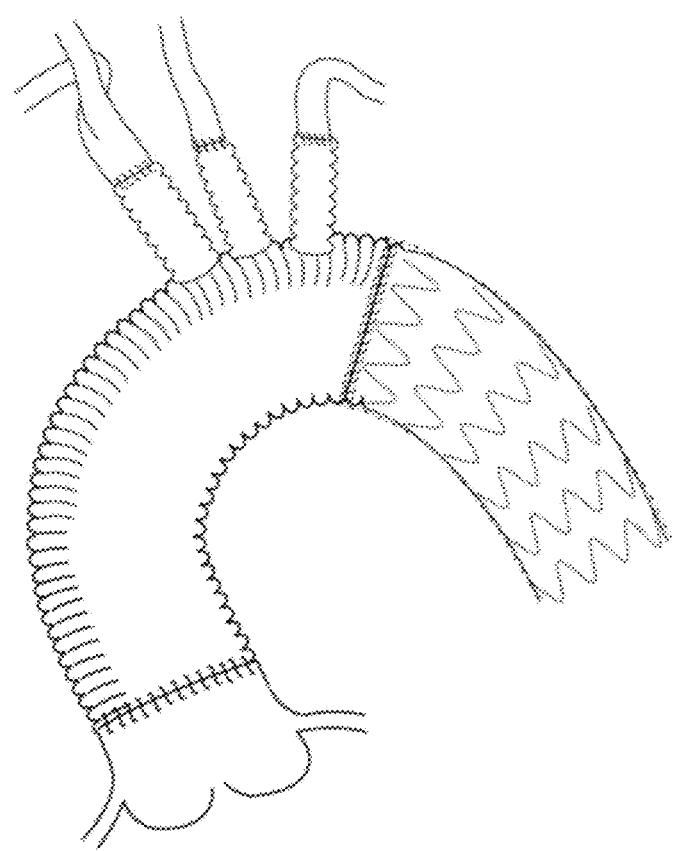
FIG. 5 illustrates a schematic diagram of the artificial blood vessel according to an embodiment of the present disclosure.

As illustrated in FIGS. 3 to 5, the driving mechanism 3 is detachably arranged at the rear end of the spiral suturing needle 2, configured to rotate the spiral suturing needle 2 into the groove 11. The driving mechanism 3 includes a driving wheel 31, a needle penetration rod 32 and a variable aperture baffle 33, and an eccentric through hole is arranged on the driving wheel 31, and the distance between the center of the driving wheel 31 and the eccentric through hole on the driving wheel 31 is equal to the radius of the spiral suturing needle 2, and one end of the needle penetration rod 32 is fixedly connected to the center of the driving wheel 31, the variable aperture baffle 33 is arranged on one side of the needle penetration rod 32, and the distance between the variable aperture baffle 33 and the driving wheel 31 is equal to the compression length of the spiral suturing needle 2. When the driving mechanism 3 is operating, the rear end of the spiral suturing needle 2 passes through the eccentric through hole, and the whole of the spiral suturing needle 2 is sheathed on the needle penetration rod 32, and is compressed behind the variable aperture baffle 33, and then the front portion of the spiral suturing needle 2 keeps rotating out of the variable aperture baffle 33 with the rotation of the driving wheel 31. The recovery mechanism 4 is detachably arranged at the front end of the spiral suturing needle 2, and configured to rotate the spiral suturing needle 2 out of the groove 11. The recovery mechanism 4 includes a recovery wheel, and the thickness of the recovery wheel is equal to the distance between two adjacent helices of the spiral suturing needle 2 without deformation. An eccentric through hole is arranged on the recovery wheel, and the distance between the center of the recovery wheel and the eccentric through hole on the recovery wheel is equal to the radius of the spiral suturing needle 2. When the recovery mechanism 4 is operating, the front portion of the spiral suturing needle 2 is passed through the eccentric through hole, the spiral suturing needle 2 constantly pierces out of the eccentric through hole along with the rotation of the recovery wheel. The suture-taking-up mechanism 5 is arranged along the path of the groove 11, which can be arranged at the inflection point of the groove 11. The suture-taking-up mechanism 5 has a hook-shaped end, which is configured to take up the suture for tightening. The suture-taking-up mechanism 5 includes a suture-taking-up shaft 51 and a suture-taking-up hook 52, and the middle portion of the suture-taking-up hook 52 is hinged with the suture-taking-up shaft 51. The hook-shaped portion at the front of the suture-taking-up hook 52 can catch the sutures by turning the rear end of the suture-taking-up hook 52, and the suture can be pulled and tightened by moving the suture-taking-up shaft 51. The suture-feeding mechanism 6 is arranged proximity to the tail portion of the spiral suturing needle 2, and configured to feed the suture. The suture feeding mechanism 6 includes the suture-winding shaft 61, the spring crimper 62 and the connecting rod 63, two ends of the connecting rod 63 are respectively connected to the suture-winding shaft 61 and the driving wheel 31, and the spring crimper 62 is arranged on the connecting rod 63 that can be specifically realized by a machine head of an embroidery rotary machine. The knotting mechanism is arranged at the portion where the two ends of the adjacent suture line coincide and configured to knot the suture, which already realized by an automatic joint apparatus through the spinning technologies in textile field.

The present disclosure further provides the method for suturing the path by utilizing the apparatus. The apparatus includes the following steps.

In S1, the metallic stent to be sutured is embedded into the groove 11, such that the metallic stent can be located proximate to the center of the groove 11, and then the inner strut 1 is sheathed inside the sutured material to stretch the sutured material, the driving mechanism 3 is installed at the rear end of the spiral suturing needle 2 and compresses the spiral suturing needle 2.

In S2, the spiral suturing needle 2 is rotated by the driving mechanism 3, to enable the suturing needle tip 21 to repeat the process of piercing into the sutured material, bypassing the metal wire of the metallic stent, and piercing out of the sutured material; so that the compressed spiral suturing needle 2 recoveries elasticity with the rotating action and continuously moving forward along the path of the groove 11.

In S3, after the spiral suturing needle 2 completes the process along the path, the suturing needle tip 21 is rotated out of the groove 11, then the action of the driving mechanism 3 is disabled, the recovery mechanism 4 is installed at the front end of the spiral suturing needle, and the suture is provided to suture-piercing hole by the suture-feeding mechanism.

In S4, the spiral suturing needle 2 is rotated by the recovery mechanism 4 in the same rotating direction as the driving mechanism 3, so that the spiral suturing needle 2 is rotated out of the groove 11 and the metallic stent and the sutured material is bound by using the suture at the tail portion of the spiral suturing needle 2.

In S5, the suture is taken up by the suture-taking-up mechanism 5 on the path of the groove 11, and then the suture is tightened by the recovery mechanism 4, and the taking-up and tightening operations are repeated to effectively prevent the suture from being stuck or broken due to the increased friction after the continuous entry of the suture.

In S6, the spiral suturing needle 2 and the recovery mechanism 4 are removed after the rear end of the spiral suturing needle 2 is rotated out of the groove 11. Since the starting end and the tail end of the suture coincide with each other after a circle of suturing, and the two ends of the suture can be knotted through the knotting mechanism by leaving a length of free suture at each of the starting end and the tail end so as to complete the suturing along the path.

To sum up, the present disclosure can realize the sutures of small-diameter objects prepared by flexible materials along the paths, and solves the problem of difficulties in suturing the artificial blood vessels and similar scenarios along the paths, and the whole process can be automated and unmanned, which solves the most critical technical problems for the subsequent intelligent development.

What is claimed is:

1. An apparatus for suturing along a path, comprising:
    an inner strut,
    a spiral suturing needle,
    a driving mechanism,
    a recovery mechanism,
    a suture-taking-up mechanism, and
    a suture-feeding mechanism; wherein
    the inner strut is sheathed inside a sutured material to be sutured, and a metallic stent to be sutured is arranged in an artificial blood vessel, grooves are distributed on periphery with respect to an axial direction of the inner strut, and a path of the groove is consistent with a path of the metallic stent to be sutured, and a width of the groove matches an outer diameter of the spiral suturing needle;
    embedded threaded channels are arranged in the grooves, which can constrain the spiral suturing needle to advance forward according to a track of the threaded channels;
    the spiral suturing needle is an elastic retractable structure and a length of the spiral suturing needle without deformation is longer than a length of the path of the groove, and a suturing needle tip is arranged on a head portion of the spiral suturing needle and a suture-piercing hole is arranged on a tail portion of the spiral suturing needle;
    the driving mechanism is detachably arranged at a rear end of the spiral suturing needle, the driving mechanism includes a driving wheel, a needle penetration rod and a variable aperture baffle, and an eccentric through hole is arranged on the driving wheel, one end of the needle penetration rod is fixedly connected to a center of the driving wheel, the variable aperture baffle is arranged on one side of the needle penetration rod, a distance between the variable aperture baffle and the driving wheel is equal to a compression length of the spiral suturing needle, the rear end of the spiral suturing needle passes through the eccentric through hole, and the whole of the spiral suturing needle is sheathed on the needle penetration rod, and is compressed behind the variable aperture baffle, and then a front portion of the spiral suturing needle keeps rotating out of the variable aperture baffle with the rotation of the driving wheel;
    the recovery mechanism is detachably arranged at a front end of the spiral suturing needle, the recovery mechanism includes a recovery wheel on which an eccentric through hole is arranged and a thickness of which is equal to a distance between two adjacent helices of the spiral suturing needle without deformation, the front portion of the spiral suturing needle is passed through the eccentric through hole, the spiral suturing needle constantly pierces out of the eccentric through hole along with the rotation of the recovery wheel, and a rotating direction of the recovery mechanism is the same as the driving mechanism;
    the suture-taking-up mechanism with a hook-shaped end is arranged along a path direction of the groove;
    the suture-feeding mechanism is arranged at the tail portion of the spiral suturing needle, the suture-feeding mechanism includes a suture-winding shaft, a spring crimper and a connecting rod, two ends of the connecting rod are connected with the suture-winding shaft and the driving wheel respectively, and the spring crimper is arranged on the connecting rod.

2. The apparatus for suturing along the path according to claim 1, wherein
    the suture-taking-up mechanism includes
        a suture-taking-up shaft, and
        a suture-taking-up hook, which is corresponding to the hook-shaped end, and
    a middle portion of the suture-taking-up hook is hinged with the suture-taking-up shaft.

3. The apparatus for suturing along the path according to claim 1, wherein
    a distance between the center of the driving wheel and the eccentric through hole on the driving wheel is equal to a radius of the spiral suturing needle; and
    a distance between a center of the recovery wheel and the eccentric through hole on the recovery wheel is equal to the radius of the spiral suturing needle.

4. The apparatus for suturing along the path according to claim 1, wherein a depth of the groove is greater than ⅔ a length of the outer diameter of the spiral suturing needle.

5. The apparatus for suturing along the path according to claim 1, wherein the suture-taking-up mechanism is arranged at an inflection point of the groove.

6. The apparatus for suturing along the path according to claim 1, wherein an inner diameter of the spiral suturing needle is greater than a diameter of the metallic stent.

7. A method for suturing along a path by utilizing the apparatus according to claim 1, comprising following steps:
    S1, embedding the metallic stent to be sutured into the groove, and then sheathing the inner strut inside the sutured material, installing the driving mechanism at the rear end of the spiral suturing needle and compressing the spiral suturing needle;
    S2, rotating, by the driving mechanism, the spiral suturing needle, to enable the suturing needle tip to repeat a process of piercing into the sutured material, bypassing a metal wire of the metallic stent, and piercing out of the sutured material, so that the compressed spiral suturing needle recoveries elasticity with the rotating action and continuously moving forward along the path of the groove;
    S3, rotating, after the spiral suturing needle completes the process along the path, the suturing needle tip out of the groove, disabling the action of the driving mechanism, installing the recovery mechanism at the front end of the spiral suturing needle, and providing, by the suture-feeding mechanism, the suture to the suture-piercing hole;
    S4, rotating, by the recovery mechanism, the spiral suturing needle, so that the spiral suturing needle is rotated out of the groove, and binding, by using the suture at the tail portion of the spiral suturing needle, the metallic stent and the sutured material;
    S5, taking up, by the suture-taking-up mechanism on the path of the groove, the suture, tightening, by the recovery mechanism and the suture-feeding mechanism, the suture, and repeating the taking-up and tightening operations; and S6, removing, after the rear end of the spiral suturing needle is rotated out of the groove, the spiral suturing needle and the recovery mechanism, knotting two ends of the suture to complete the suturing around the path.

\* \* \* \* \*